United States Patent
Wang et al.

(10) Patent No.: US 9,556,221 B2
(45) Date of Patent: Jan. 31, 2017

(54) N-ACETYL AMINO ACID ESTER DERIVATIVES OF BETULIN AND PREPARATION METHOD THEREOF

(71) Applicant: Northeast Forestry University, Heilongjiang (CN)

(72) Inventors: Yang Wang, Heilongjiang (CN); Sheng Zhang, Heilongjiang (CN); Weiming Ding, Heilongjiang (CN); Tao Yu, Heilongjiang (CN); Xiufeng Yan, Heilongjiang (CN)

(73) Assignee: Northeast Forestry University, Heilongjiang (CN)

( * ) Notice: Subject to any disclaimer, the term of this patent is extended or adjusted under 35 U.S.C. 154(b) by 37 days.

(21) Appl. No.: 14/598,842

(22) Filed: Jan. 16, 2015

(65) Prior Publication Data

US 2015/0368291 A1 Dec. 24, 2015

(30) Foreign Application Priority Data

Jun. 20, 2014 (CN) .......................... 2014 1 0281027

(51) Int. Cl.
*C07J 53/00* (2006.01)
*C07J 63/00* (2006.01)
(52) U.S. Cl.
CPC .................... *C07J 63/008* (2013.01)
(58) Field of Classification Search
CPC ....................................................... C07J 53/002
USPC ......................................... 548/528; 552/510
See application file for complete search history.

(56) References Cited

U.S. PATENT DOCUMENTS 5,468,888 A 11/1995 Bouboutou et al.

FOREIGN PATENT DOCUMENTS

WO 2008070347 6/2008
WO 2008127364 10/2008

OTHER PUBLICATIONS

Tang Jun eta!., "Selective oxidation of betulin for betulinic acid preparation", Journal of Dalian Polytechnic University, Jul. 2009, vol. 28, No. 4, pp. 244-247.
Zhu Wei, "Application technology and development of dibronnohydantoin", China New Technologies and Products, Feb. 2011, No. 2, p. 150 (abstract translated with Google translate).
Zhong Ping etal., "Synthesis and application of trichloroiminocyanuric acid", Chemical Reagents, 2003, vol. 25, No. 1, pp. 15-17.
Zaragoza Dorwald (Side Reactions in Organic Synthesis, 2005, WILEY-VCH Verlag GmbH & Co. KGaA, Weinheim, Preface. p. IX.
Barthel et al, Tetrahedron, Oxidative Transformations of Betulinol, 2008, 64, pp. 9225-9229.

*Primary Examiner* — Brenda Coleman
(74) *Attorney, Agent, or Firm* — Vidas, Arrett & Steinkraus, P.A.

(57) ABSTRACT

The present invention disclosed N-acetyl amino acid ester derivatives of betulin and the preparation method thereof, the method comprising the steps that in the presence of an alkaline substance, a catalyst and a racemization-inhibitor, the carboxyl group of N-acetyl amino acid is activated by a coupling agent; and then the activated N-acetyl amino acid is reacted with betulin via esterification reaction to obtain the N-acetyl amino acid ester derivative of betulin. The present invention provided a simple synthesis method to synthesize the N-acetyl amino acid ester derivatives of betulin by using betulin as a precursor compound and modifying the molecular structure of betulin. Such structural modification of betulin significantly enhances the anti-tumor activity of the betulin derivatives and therefore has important values.

10 Claims, No Drawings

N-ACETYL AMINO ACID ESTER DERIVATIVES OF BETULIN AND PREPARATION METHOD THEREOF

CROSS-REFERENCE TO RELATED APPLICATIONS

This application claims the benefit of Chinese patent application no. 201410281027.2, filed Jun. 20, 2014, the entire content of which is hereby incorporated herein by reference.

TECHNICAL FIELD OF THE INVENTION

The present invention relates to the field of pharmaceutical chemistry and therapeutics, more particularly to N-acetyl amino acid ester derivatives of betulin and the preparation method thereof.

BACKGROUND

Betulin (also known as Lup-20(29)-ene-3β,28-diol or betulinol) is a needle-like crystal with a molecular formula of $C_{30}H_{50}O_2$, a molecular weight of 442.70, and a molecular structure as below:

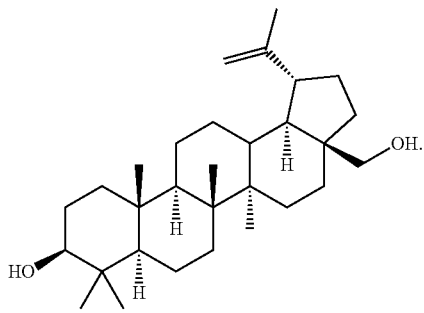

Betulin is a pentacyclic triterpenoid of lupane structure, the content of which in the bark of birch tree can reach up to 40%. Betulinic acid which is a betulin derivative shows unique anti-tumor activity and is substantially non-toxic, and thus some novel derivatives synthesized from betulinic acid as a precursor compound have been extensively studied.

Unlike betulinic acid, betulin itself has poor anti-tumor activity, but its price is low as only 10% of that of betulinic acid. Therefore, it has important value for semi-synthesis from betulin as a precursor to look for new derivatives which have superior anti-tumor activity.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

An object of the present invention is to provide an N-acetyl amino acid ester derivative of betulin and the preparation method thereof, for enhancing the anti-tumor activity of the betulin derivatives.

To achieve the above object, the present invention provides an N-acetyl amino acid ester derivative of betulin with the following structural formula:

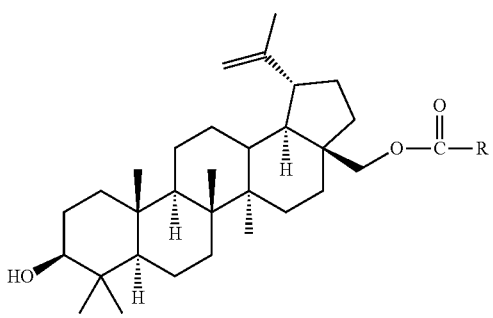

wherein, R is selected from one of

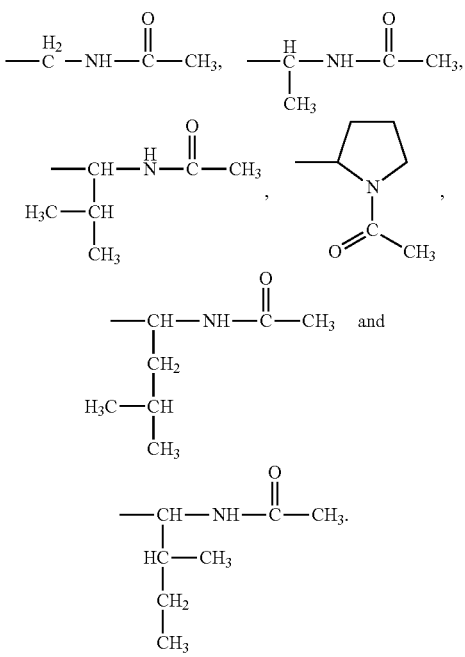

The present invention also provides a method for preparing the N-acetyl amino acid ester derivative of betulin, comprising the following steps:

a) in the presence of an alkaline substance, a catalyst and a racemization-inhibitor, the carboxyl group of N-acetyl amino acid is activated by a coupling agent; and then b) the activated N-acetyl amino acid is reacted with betulin via esterification reaction to obtain the N-acetyl amino acid ester derivative of betulin.

Preferably, the method for preparing the N-acetyl amino acid ester derivative of betulin particularly comprises the following steps: a N-acetyl amino acid, an alkaline substance, a catalyst and a racemization-inhibitor are added into an organic reagent, and a coupling agent is added after adequate stirring, to react for 0.5 to 4 hours at 20~50° C. under nitrogen, and then betulin is added to react for 8 to 24 hours at 20~50° C., thereby to obtain the N-acetyl amino acid ester derivative of betulin.

Preferably, the method further comprises the purification step of the N-acetyl amino acid ester derivative of betulin, including: after completion of the reaction, the reaction solution is added dropwise into distilled water to form a solution with precipitate; the solution is filtered under suction to give a solid precipitate, and then the solid precipitate is purified via silica gel column chromatography after drying, thereby to obtain the purified N-acetyl amino acid ester derivative of betulin.

Optionally, the organic reagent is selected from N, N-dimethylacetamide.

Preferably, the alkaline substance is selected from N-ethyldiisopropylamine.

Optionally, the catalyst is selected from 4-dimethylaminopyridine.

Preferably, the racemization-inhibitor is selected from 1-hydroxybenzotriazole.

Optionally, the coupling agent is selected from 1-(3-dimethylaminopropyl)-3-ethyl carbodiimide hydrochloride.

Preferably, the N-acetyl amino acid is selected from one of N-acetyl-glycine, N-acetyl-alanine, N-acetyl-valine, N-acetyl-proline, N-acetyl-leucine and N-acetyl-isoleucine.

As can be seen from the above, the present invention discloses a simple synthesis method to synthesize the N-acetyl amino acid ester derivatives of betulin by using betulin as a precursor compound and modifying the molecular structure of betulin. Such structural modification of betulin significantly enhances the anti-tumor activity of the betulin derivatives and therefore has important values.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

DESCRIPTION OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The present invention is further described in combination of the following examples in details.

The present invention provides an N-acetyl amino acid ester derivative of betulin, with the following structural formula:

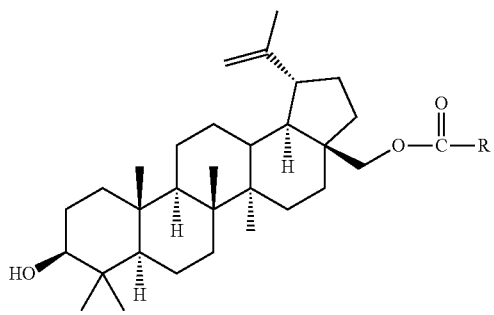

Wherein, R is selected from one of

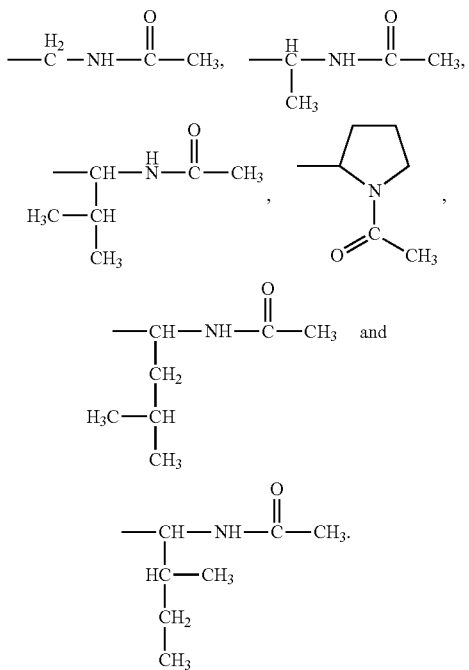

The specific derivatives synthesized by the present invention are shown in Table 1.

TABLE 1

| No. of the derivatives | R |
|---|---|
| YWZ-001 | —CH₂—NH—C(O)—CH₃ |
| YWZ-002 | —CH(CH₃)—NH—C(O)—CH₃ |
| YWZ-003 | —CH(CH(CH₃)₂)—NH—C(O)—CH₃ |
| YWZ-004 | pyrrolidine-N-C(O)CH₃ |
| YWZ-005 | —CH(CH₂CH(CH₃)₂)—NH—C(O)—CH₃ |

TABLE 1-continued

| No. of the derivatives | R |
|---|---|
| YWZ-006 | 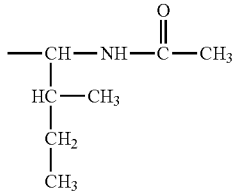 |

The present invention also provides a method for preparing N-acetyl amino acid ester derivative of betulin, comprising the following steps: in the presence of an alkaline substance, a catalyst and a racemization-inhibitor, the carboxyl group of N-acetyl amino acid is activated by a coupling agent; and then the activated N-acetyl amino acid is reacted with betulin via esterification reaction to obtain the N-acetyl amino acid ester derivative of betulin.

Specifically, the method for preparing the N-acetyl amino acid ester derivative of betulin particularly comprises that a N-acetyl amino acid, an alkaline substance, a catalyst and a racemization-inhibitor are added into an organic solvent, and a coupling agent is added after adequate stirring, to react for 0.5 to 4 hours at 20~50° C. under nitrogen; and then betulin is added to react for 8 to 24 hours at 20~50° C., thereby to obtain the N-acetyl amino acid ester derivative of betulin.

In an embodiment of the invention, the method further comprises the purification step of the N-acetyl amino acid ester derivative of betulin, including: after completion of the reaction, the reaction solution is added dropwise into distilled water to form a solution with precipitate; the solution is filtered under suction to give a solid precipitate, and then the solid precipitate is purified via silica gel column chromatography after drying, thereby to obtain the purified N-acetyl amino acid ester derivative of betulin.

In another embodiment of the invention, the organic solvent is selected from N, N-dimethylacetamide.

In another embodiment of the invention, the alkaline substance is selected from N-ethyldiisopropylamine.

In another embodiment of the invention, the catalyst is selected from 4-dimethylaminopyridine.

In another embodiment of the invention, the racemization-inhibitor is selected from 1-hydroxybenzotriazole.

In another embodiment of the invention, the coupling agent is selected from 1-(3-dimethylaminopropyl)-3-ethyl carbodiimide hydrochloride.

In another embodiment of the invention, the N-acetyl amino acid is selected from one of N-acetyl-glycine, N-acetyl-alanine, N-acetyl-valine, N-acetyl-proline, N-acetyl-leucine and N-acetyl-isoleucine.

EXAMPLES

Example 1

Preparation of the Derivative YWZ-001

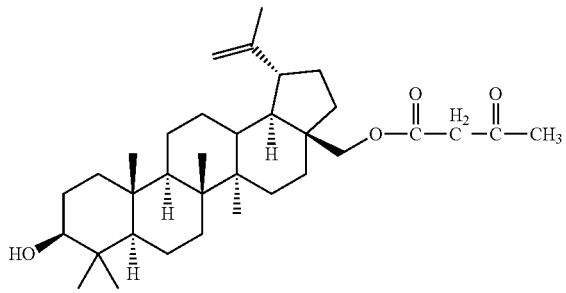

1 mmol of N-acetyl-glycine, 1.2 mmol of 1-hydroxybenzotriazole (HOBT), 0.1 mmol of 4-dimethylaminopyridine (DMAP) and 3 mmol N-ethyldiisopropylamine (DIPEA) were added into 5 ml of N,N-dimethylacetamide (DMAC) under magnetic stirring, and then 1 mmol of 1-(3-dimethylaminopropyl)-3-ethylcarbodiimide hydrochloride (ED-C.HCl) was added under nitrogen to react for 1 hr at 25° C. for activating the carboxyl group of N-acetyl-glycine.

Then, 1.0 mmol of betulin was added thereinto and reacted for 12 hrs at 25° C. After completion of the reaction, the reaction solution was added dropwise into 250 ml of distilled water to form a solution with precipitation and the solution was filtered under suction to give a solid precipitate, and then the solid precipitate was dried in a blast oven at 60° C. and purified via silica gel column chromatography (petroleum ether:ethyl acetate=2:1 (volume)) to give 0.35 g of white solid of N-acetyl amino acid ester derivative of betulin YWZ-1, with a yield of 65%. Melting point (mp): 216~217° C.; Mass spectrometry ESI-MS: m/z 541 [MH]−.

$^1$H NMR (400 MHz, CDCl$_3$): δ 4.68 (s, 1H, H-29a), 4.59 (s, 1H, H-29b), 4.37 (d, J=10.9 Hz, 1H, H-28$_a$), 4.07 (d, J=5.0 Hz, 2H, H-2'), 3.92 (d, J=10.9 Hz, 1H, H-28b), 3.18 (dd, J$_1$=4.8 Hz, J$_2$=4.8 Hz, 1H, H-3), 2.43 (dt, J$_1$=5.9 Hz, J$_2$=5.7 Hz, J$_3$=5.8 Hz, 1H, H-19), 2.05 (s, 3H, H-4'), 1.67 (s, 3H, H-30), 1.02 (s, 3H), 0.97 (s, 3H), 0.96 (s, 3H), 0.81 (s, 3H), 0.75 (s, 3H).

$^{13}$C NMR (75 MHz, CDCl$_3$): δ 170.66, 170.32, 150.01, 110.07, 78.97, 64.01, 55.34, 50.39, 48.82, 47.76, 46.52, 42.76, 41.50, 40.93, 38.93, 38.78, 37.70, 37.20, 34.52, 34.23, 29.69, 29.56, 28.07, 27.44, 27.08, 25.21, 23.06, 20.82, 19.18, 18.34, 16.18, 16.07, 15.47, 14.84.

Example 2

Preparation of the Derivative YWZ-002

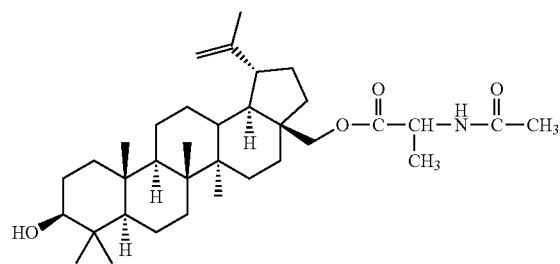

1 mmol of N-acetyl-alanine, 2 mmol of 1-hydroxybenzotriazole (HOBT), 0.2 mmol of 4-dimethylaminopyridine (DMAP) and 2 mmol N-ethyldiisopropylamine (DIPEA) were added into 8 ml of N,N-dimethylacetamide (DMAC) under magnetic stirring, and then 1.5 mmol of 1-(3-dimethylaminopropyl)-3-ethylcarbodiimide hydrochloride (EDC.HCl) was added under nitrogen to react for 1.5 hrs at 20° C. for activating the carboxyl group of N-acetyl-alanine.

Then, 1.1 mmol of betulin was added thereinto and reacted for 10 hrs at 20° C. After completion of the reaction, the reaction solution was added dropwise into 280 ml of distilled water to form a solution with precipitation and the solution was filtered under suction to give a solid precipitate, and then the solid precipitate was dried in a blast oven at 40° C. and purified via silica gel column chromatography (petroleum ether:ethyl acetate=5:1 (volume)) to give white solid of N-acetyl amino acid ester derivative of betulin YWZ-002, with a yield of 70%. Melting point (mp): 213~214° C.; Mass spectrometry ESI-MS: m/z 555 [MH]⁻.

$^1$H NMR (400 MHz, CDCl$_3$): δ 4.68 (s, 1H, H-29a), 4.62 (m, 1H, H-2'), 4.59 (s, 1H, H-29b), 4.43 (d, J=11.0 Hz, 1H, H-28a), 3.85 (d, J=10.8 Hz, 1H, H-28b), 3.18 (m, 1H, H-3), 2.42 (dt, 71=5.9 Hz, 72=5.6 Hz, 73=5.8 Hz, 1H, H-19), 2.02 (s, 3H, H-4'), 1.67 (s, 3H, H-30), 1.42 (d, J=7.1 Hz, 3H, H-5'), 1.03 (s, 3H), 0.97 (s, 3H), 0.96 (s, 3H), 0.82 (s, 3H), 0.75 (s, 3H).

$^{13}$C NMR (75 MHz, CDCl$_3$): δ 173.76, 169.63, 150.07, 110.10, 79.05, 63.96, 55.39, 50.44, 48.91, 48.32, 47.82, 46.68, 42.82, 40.97, 38.98, 38.81, 37.75, 37.26, 34.57, 34.26, 29.80, 29.62, 28.11, 27.50, 27.10, 25.27, 23.34, 20.87, 19.25, 18.92, 18.38, 16.22, 16.10, 15.50, 14.90.

Example 3

Preparation of the Derivative YWZ-003

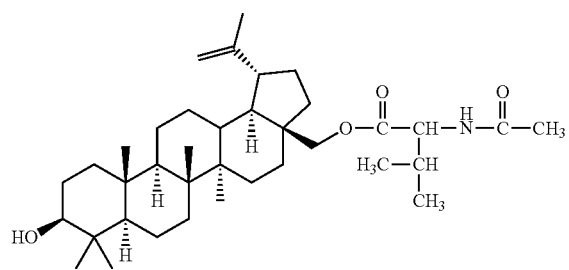

1 mmol of N-acetyl-valine, 2 mmol of 1-hydroxybenzotriazole (HOBT), 0.3 mmol of 4-dimethylaminopyridine (DMAP) and 2.5 mmol N-ethyldiisopropylamine (DIPEA) were added into 4 ml of N,N-dimethylacetamide (DMAC) under magnetic stirring, and then 2 mmol of 1-(3-dimethylaminopropyl)-3-ethylcarbodiimide hydrochloride (EDC.HCl) was added under nitrogen to react for 4 hrs at 40° C. for activating the carboxyl group of N-acetyl-valine.

Then, 1.0 mmol of betulin was added thereinto and reacted for 24 hrs at 40° C. After completion of the reaction, the reaction solution was added dropwise into 240 ml of distilled water to form a solution with precipitation and the solution was filtered under suction to give a solid precipitate, and then the solid precipitate was dried in a blast oven at 60° C. and purified via silica gel column chromatography (petroleum ether:ethyl acetate=1:2 (volume)) to give white solid of N-acetyl amino acid derivative of betulin YWZ-003, with a yield of 51%. Melting point (mp): 184~186° C.; Mass spectrometry ESI-MS: m/z 583 [MH]⁻.

$^1$H NMR (400 MHz, CDCl$_3$): δ 4.69 (s, 1H, H-29a), 4.62 (m, 1H, H-2'), 4.59 (s, 1H, H-29b), 4.34 (m, 1H, H-28a), 3.86 (m, 1H, H-28b), 3.72 (m, 1H, H-5'), 3.18 (m, 1H, H-3), 2.42 (dt, J$_1$=5.4 Hz, J$_2$=5.2 Hz, J$_3$=5.5 Hz, 1H, H-19), 2.05 (s, 3H, H-4'), 1.68 (s, 3H, H-30), 1.02 (s, 3H), 0.97 (s, 3H), 0.96 (s, 3H), 0.95 (d, J=8.7 Hz, 3H, H-6'), 0.90 (d, J=6.8 Hz, 3H, H-7'), 0.82 (s, 3H), 0.75 (s, 3H).

$^{13}$C NMR (75 MHz, CDCl$_3$): δ 172.85, 170.09, 150.04, 110.06, 78.98, 63.94, 55.36, 50.42, 48.87, 48.83, 46.42, 42.77, 40.94, 38.94, 37.73, 37.21, 34.23, 31.56, 31.49, 29.58, 28.08, 27.46, 25.24, 23.40, 23.38, 20.84, 19.24, 19.10, 19.06, 18.33, 17.86, 16.19, 16.09, 16.04, 15.48, 14.89, 14.85.

Example 4

Preparation of the Derivative YWZ-004

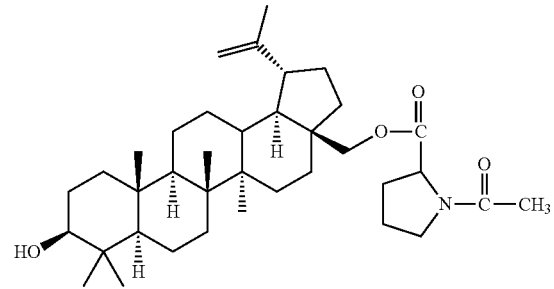

2 mmol of N-acetyl-proline, 2 mmol of 1-hydroxybenzotriazole (HOBT), 0.2 mmol of 4-dimethylaminopyridine (DMAP) and 5 mmol N-ethyldiisopropylamine (DIPEA) were added into 5 ml of N,N-dimethylacetamide (DMAC) under magnetic stirring, and then 2 mmol of 1-(3-dimethylaminopropyl)-3-ethylcarbodiimide hydrochloride (EDC.HCl) was added under nitrogen to react for 3.5 hrs at 50° C. for activating the carboxyl group of N-acetyl-proline.

Then, 1.0 mmol of betulin was added thereinto and reacted for 16 hrs at 50° C. After completion of the reaction, the reaction solution was added dropwise into 260 ml of distilled water to form a solution with precipitate and the solution was filtered under suction to give a solid precipitate, then the solid precipitate was dried in a blast oven at 55° C. and purified via silica gel column chromatography (chloroform:methanol=10:1 (volume)) to give white solid of N-acetyl amino acid ester derivative of betulin YWZ-004, with a yield of 55%. Melting point (mp): 204~206° C.; Mass spectrometry ESI-MS: m/z 581 [MH]⁻.

$^1$H NMR (400 MHz, CDCl$_3$): δ 4.67 (s, 1H, H-29a), 4.57 (s, 1H, H-29b), 4.50 (m, 1H, H-2'), 4.39 (d, J=11.0 Hz, 1H, H-28a), 3.89 (d, J=10.8 Hz, 1H, H-28b), 3.64 (m, 1H, H-7'a), 3.49 (m, 1H, H-7'b), 3.17 (m, 1H, H-3), 2.42 (dt, J$_1$=6.4 Hz, J$_2$=5.7 Hz, J$_3$=5.8 Hz, 1H, H-19), 2.19 (m, 1H, H-5'a), 2.08 (s, 3H, H-4'), 2.02 (m, 1H, H-5'b), 1.97 (m, 1H, H-6'a), 1.83 (m, 1H, H-6'b), 1.67 (s, 3H, H-30), 1.02 (s, 3H), 0.96 (s, 3H), 0.95 (s, 3H), 0.81 (s, 3H), 0.75 (s, 3H).

$^{13}$C NMR (75 MHz, CDCl$_3$): δ 172.86, 169.40, 150.26, 109.92, 79.02, 63.28, 58.85, 55.41, 50.47, 48.97, 47.85, 47.81, 46.75, 42.80, 40.97, 38.98, 38.82, 37.71, 37.25, 34.61, 34.24, 31.74, 29.91, 29.73, 28.12, 27.51, 27.13, 25.32, 24.96, 22.38, 20.87, 19.32, 18.38, 16.22, 16.12, 15.52, 14.90.

Example 5

Preparation of the Derivative YWZ-005

YWZ-005

1.5 mmol of N-acetyl-leucine, 1.5 mmol of 1-hydroxybenzotriazole (HOBT), 0.15 mmol of 4-dimethylaminopyridine (DMAP) and 4 mmol N-ethyldiisopropylamine (DIPEA) were added into 7 ml of N,N-dimethylacetamide (DMAC) under magnetic stirring, and then 2 mmol of 1-(3-dimethylaminopropyl)-3-ethylcarbodiimide hydrochloride (EDC.HCl) was added under nitrogen to react for 1.0 hr at 25° C. for activating the carboxyl group of N-acetyl-leucine.

Then, 1.0 mmol of betulin was added thereinto and reacted for 5 hrs at 25° C. After completion of the reaction, the reaction solution was added dropwise into 258 ml of distilled water to form a solution with precipitate and the solution was filtered under suction to give a solid precipitate, and then the solid precipitate was dried in a blast oven at 45° C. and purified via silica gel column chromatography (chloroform:methanol=20:1 (volume)) to give white solid of N-acetyl amino acid ester derivative of betulin YWZ-005, with a yield of 40%. Melting point (mp): 142~144° C.; Mass spectrometry ESI-MS: m/z 597 [MH]$^-$.

$^1$H NMR (400 MHz, CDCl$_3$): δ 4.69 (s, 1H, H-29a), 4.67 (m, 1H, H-2'), 4.59 (s, 1H, H-29b), 4.33 (m, 1H, H-28a), 3.87 (m, 1H, H-28b), 3.18 (m, 1H, H-3), 2.43 (m, 1H, H-19), 2.02 (s, 3H, H-4'), 1.68 (s, 3H, H-30), 1.63 (m, 2H, H-5'), 1.56 (m, 1H, H-6'), 1.02 (s, 3H), 0.97 (s, 3H), 0.96 (s, 3H), 0.95 (d, J=5.5 Hz, 3H, H-7'), 0.94 (d, J=4.0 Hz, 3H, H-8'), 0.82 (s, 3H), 0.76 (s, 3H).

$^{13}$C NMR (75 MHz, CDCl$_3$): δ 173.88, 169.86, 150.09, 110.06, 79.01, 63.93, 55.37, 50.94, 48.87, 47.78, 46.53, 42.78, 42.09, 40.95, 38.95, 38.80, 37.72, 37.23, 34.62, 34.24, 29.62, 28.09, 27.48, 27.10, 25.26, 25.02, 23.33, 22.90, 22.26, 20.85, 19.24, 18.37, 16.20, 16.10, 15.49, 14.88, 14.87.

Example 6

Preparation of the Derivative YWZ-006

YWZ-006

1.8 mmol of N-acetyl-isoleucine, 1.8 mmol of 1-hydroxybenzotriazole (HOBT), 0.18 mmol of 4-dimethylaminopyridine (DMAP) and 5 mmol N-ethyldiisopropylamine (DIPEA) were added into 6.5 ml of N,N-dimethylacetamide (DMAC) under magnetic stirring, and then 1.8 mmol of 1-(3-dimethylaminopropyl)-3-ethylcarbodiimide hydrochloride (EDC.HCl) was added under nitrogen to react for 3 hrs at 30° C. for activating the carboxyl group of N-acetyl-valine.

Then, 1.0 mmol of betulin was added thereinto and reacted for 10 hrs at 30° C. After completion of the reaction, the reaction solution was added dropwise into 220 ml of distilled water to form a solution with precipitate and the solution was filtered under suction to give a solid precipitate, and then the solid precipitate was dried in a blast oven at 35° C. and purified via silica gel column chromatography (chloroform:methanol=8:1 (volume)) to give white solid of N-acetyl amino acid ester derivative of betulin YWZ-006, with a yield of 42%. Melting point (mp): 188~190° C.; Mass spectrometry ESI-MS: m/z 597 [MH]$^-$.

$^1$H NMR (400 MHz, CDCl$_3$): δ 4.75 (m, 1H, H-2'), 4.69 (s, 1H, H-29a), 4.59 (s, 1H, H-29b), 4.32 (m, 1H, H-28a), 3.86 (m, 1H, H-28b), 3.18 (m, 1H, H-3), 2.43 (m, 1H, H-19), 2.04 (s, 3H, H-4'), 1.92 (m, 1H, H-5'), 1.68 (s, 3H, H-30), 1.18 (m, 2H, H-6'), 1.02 (s, 3H), 0.97 (s, 3H), 0.96 (s, 3H), 0.94 (m, 3H, H-7'), 0.86 (d, J=6.7 Hz, 3H, H-8'), 0.82 (s, 3H), 0.75 (s, 3H).

$^{13}$C NMR (75 MHz, CDCl$_3$): δ 173.15, 170.15, 150.07, 110.06, 79.02, 63.97, 55.49, 55.37, 50.43, 48.85, 47.76, 46.47, 46.38, 42.79, 40.96, 38.96, 38.80, 38.06, 37.74, 37.23, 34.69, 34.25, 29.75, 29.61, 28.09, 27.48, 26.28, 25.28, 23.44, 20.86, 19.26, 18.37, 16.20, 16.10, 15.48, 14.87, 14.78, 11.91.

The present invention also relates to the application of the N-acetyl amino acid ester derivatives of betulin for the preparation of anti-tumor drugs. By using MTT assay, experimental results of in vitro activity screening show that the N-acetyl acetyl amino acid ester derivatives of betulin provided by the present invention have significant anti-tumor effects and excellent dose-dependent manners.

Human colon tumor cell lines HT29, pancreatic cancer cell lines MPC2 and ovarian cancer cell lines MDAH2774 were selected to determine the half inhibitory concentrations (IC50s) of the N-acetyl amino acid ester derivatives of betulin, betulinic acid and betulin, and the results are shown in Table 2.

TABLE 2

The half inhibitory concentrations (IC50s) of the N-acetyl amino acid ester derivatives of betulin, betulinic acid and betulin against the three tumor cell lines.

| Compounds | IC50 (μmol/L) | | |
|---|---|---|---|
| | HT29 | MPC2 | MDAH2774 |
| YWZ-002 | 6.58 ± 0.24 | 4.24 ± 0.23 | 10.56 ± 0.62 |
| YWZ-003 | 14.09 ± 0.83 | 11.43 ± 0.89 | 10.87 ± 0.76 |
| YWZ-004 | 8.88 ± 0.62 | 5.32 ± 0.21 | 2.13 ± 0.05 |
| YWZ-005 | 18.12 ± 1.51 | 19.71 ± 0.83 | 1.38 ± 0.04 |
| YWZ-006 | 15.03 ± 1.31 | 10.17 ± 0.69 | 7.26 ± 0.10 |
| Betulinic acid | 32.66 ± 0.62 | 38.58 ± 2.91 | 39.54 ± 2.19 |
| Betulin | >100 | >100 | >100 |

As can be seen from Table 2, the N-acetyl amino acid ester derivatives of betulin provided by the present invention have very significant anti-tumor effects, especially for human colon cancer cell line HT29, pancreatic cancer cell lines MPC2 and ovarian cancer cell lines MDAH2774.

Therefore, the present invention provided a simple synthesis method to synthesize the N-acetyl amino acid ester derivatives of betulin by using betulin as a precursor compound and modifying the molecular structure of betulin. Such structural modification of betulin significantly enhances the anti-tumor activity of the betulin derivatives and thereby has important value.

The persons skilled in the art should understand that preferred embodiments of the invention are described for illustration purpose but not to limit the present invention, and any modification, replacement and change within the spirit and principles of the present invention should be fallen into the scope of the present invention.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

To be claimed:

1. An N-acetyl amino acid ester derivative of betulin, wherein the derivative has the following structural formula I:

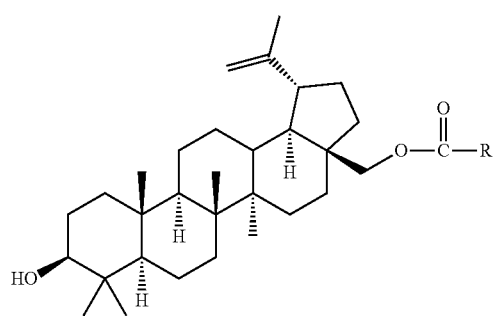

wherein R is selected from one of

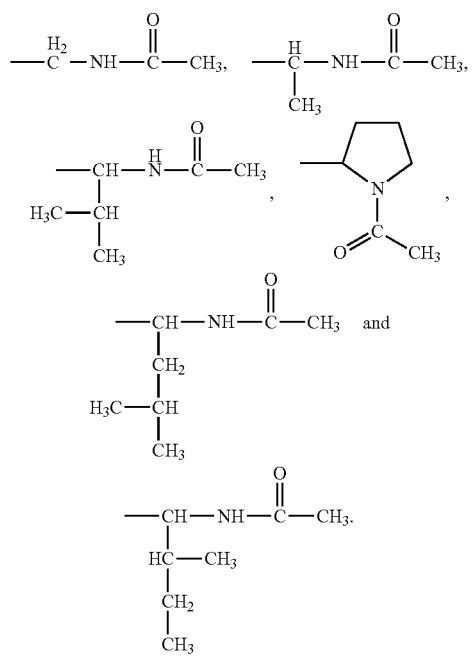

2. A method for preparing the N-acetyl amino acid ester derivative of betulin of claim 1, comprising the steps that in the presence of an alkaline substance, a catalyst and a racemization-inhibitor, the carboxyl group of N-acetyl amino acid is activated by a coupling agent; and then the activated N-acetyl amino acid is reacted with betulin via esterification reaction to obtain the N-acetyl amino acid ester derivative of betulin.

3. The method for preparing the N-acetyl amino acid ester derivative of betulin according to claim 2, further comprising the steps that a N-acetyl amino acid, an alkaline substance, a catalyst and a racemization-inhibitor are added into an organic solvent, and a coupling agent is added after adequate stirring, to react for 0.5 to 4 hours at 20~50° C. under nitrogen; and then, betulin is added to react for 8 to 24 hours at 20~50° C., thereby to obtain the N-acetyl amino acid ester derivative of betulin.

4. The method for preparing the N-acetyl amino acid ester derivative of betulin according to claim 2, further comprising the purification step of the acetyl amino acid ester derivative of betulin, including: after completion of the reaction, the reaction solution is added dropwise into the distilled water to form a solution with precipitate; the solution is filtered under suction to give a solid precipitate, and then the solid precipitate is purified via silica gel column chromatography after drying, thereby to obtain the purified N-acetyl amino acid ester derivative of betulin.

5. The method for preparing the N-acetyl amino acid ester derivative of betulin according to claim 3, wherein the organic solvent is selected from N, N-dimethylacetamide.

6. The method for preparing the N-acetyl amino acid ester derivative of betulin according to claim 2, wherein the alkaline substance is selected from N-ethyldiisopropylamine.

7. The method for preparing the N-acetyl amino acid ester derivative of betulin according to claim 2, wherein the catalyst is selected from 4-dimethylaminopyridine.

8. The method for preparing the N-acetyl amino acid ester derivative of betulin according to claim 2, wherein the racemization-inhibitor is selected from 1-hydroxybenzotriazole.

9. The method for preparing the N-acetyl amino acid ester derivative of betulin according to claim 2, wherein the coupling agent is selected from 1-(3-dimethylaminopropyl)-3-ethyl carbodiimide hydrochloride.

10. The method for preparing the N-acetyl amino acid ester derivative of betulin according to claim 2, wherein the N-acetyl amino acid is selected from one of N-acetyl-glycine, N-acetyl-alanine, N-acetyl-valine, N-acetyl-proline, N-acetyl-leucine and N-acetyl-isoleucine.

* * * * *